United States Patent
Farris et al.

(10) Patent No.: US 11,771,859 B2
(45) Date of Patent: Oct. 3, 2023

(54) LIQUID REMOVAL APPARATUS FOR A BREATHING CIRCUIT AND RELATED METHOD OF USE

(71) Applicant: Spectrum Health Innovations LLC, Grand Rapids, MI (US)

(72) Inventors: John P. Farris, Grand Rapids, MI (US); Casey S. McKellar, Grand Rapids, MI (US); Hannah N. Gorenflo, Grand Rapids, MI (US); Jonathan T. Moroney, Grand Haven, MI (US); Angelo Fusco, Wyandotte, MI (US); Travis L Dusendang, Coopersville, MI (US); Kristina H. Emery, Ravenna, MI (US); Eric J. VanMiddendorp, Rockford, MI (US); Chad M. Huizenga, Rockford, MI (US); Nelson C. Edward Schrader, Grand Rapids, MI (US)

(73) Assignees: COREWELL HEALTH INNOVATIONS LLC, Grand Rapids, MI (US); GRAND VALLEY STATE UNIVERSITY, Allendale, MI (US); KENDALL COLLEGE OF ART AND DESIGN OF FERRIS STATE UNIVERSITY, Grand Rapids, MI (US)

(*) Notice: Subject to any disclaimer, the term of this patent is extended or adjusted under 35 U.S.C. 154(b) by 638 days.

(21) Appl. No.: 16/909,720

(22) Filed: Jun. 23, 2020

(65) Prior Publication Data
US 2020/0405989 A1 Dec. 31, 2020

Related U.S. Application Data

(60) Provisional application No. 62/868,031, filed on Jun. 28, 2019.

(51) Int. Cl.
A61M 16/04 (2006.01)
A61M 16/20 (2006.01)
A61M 16/08 (2006.01)

(52) U.S. Cl.
CPC .... *A61M 16/0463* (2013.01); *A61M 16/0477* (2014.02); *A61M 16/0808* (2013.01); *A61M 16/0833* (2014.02); *A61M 16/20* (2013.01)

(58) Field of Classification Search
CPC .......... A61M 16/0477; A61M 16/0475; A61M 16/0463; A61M 16/0833; A61M 16/0808;
(Continued)

(56) References Cited

U.S. PATENT DOCUMENTS

| 4,867,153 A | 9/1989 | Lorenzen et al. |
| 5,398,677 A | 3/1995 | Smith |

(Continued)

OTHER PUBLICATIONS

Downloaded from https://avanosmedicaldevices.com/respiratory-health/endotracheal-tube-clearing-systems/ on Jun. 24, 2020 (first downloaded Jun. 12, 2018).
(Continued)

*Primary Examiner* — Joseph D. Boecker
*Assistant Examiner* — Brian T Khong
(74) *Attorney, Agent, or Firm* — Warner Norcross + Judd LLP

(57) ABSTRACT

An apparatus to remove liquid from a ventilation system can include a housing, a first port extending into an interior volume of the housing and a second port extending toward the first tube, into the interior volume, separated from the first port by a gap that is at least 5 mm in length, such that ventilating fluid transfers from the first port to the second while secretions and condensate escape through the gap, to be trapped in the housing. The first port joins with a ventilator. The second port joins with an intubation tube coupled to a tracheostomy or endotracheal tube. An extrac-
(Continued)

tion port is in a floor of the housing so that accumulated liquids in the housing can drain downward and out the extraction port, while minimizing positive end expiratory pressure loss in the ventilation system, and without exposing caregivers to biological material in the drained liquid.

20 Claims, 5 Drawing Sheets

(58) Field of Classification Search
CPC .. A61M 16/0816; A61M 16/08; A61M 16/20; A61M 16/201; A61M 16/202; A61M 16/106; A61M 16/1065; A61M 16/107; A61M 16/0875; A61M 1/75; A61M 1/60
See application file for complete search history.

(56) References Cited

U.S. PATENT DOCUMENTS

| | | | |
|---|---|---|---|
| 6,606,994 B1 * | 8/2003 | Clark | A61M 16/0808 128/205.12 |
| 8,632,624 B2 * | 1/2014 | Cassidy | A61M 5/36 604/122 |
| 2004/0020490 A1 | 2/2004 | Vogt | |
| 2004/0193100 A1 | 9/2004 | Van Hooser et al. | |
| 2004/0193101 A1 | 9/2004 | Van Hooser et al. | |
| 2011/0067699 A1 * | 3/2011 | Caruso | A61M 16/0825 128/205.29 |
| 2016/0038701 A1 * | 2/2016 | White | A61M 39/26 251/61.1 |

OTHER PUBLICATIONS

Downloaded from https://src-medical.com/inc/sdetail/endoclear_restore2__device_and_liberator_system__for_clearing_endotracheal_tubes/6367 on Jun. 24, 2020 (first downloaded Jun. 12, 2018).
http://www.ecommedicalsupplies.com/medsupplies.cfm/puritan-bennett_110870; downloaded Jun. 12, 2018.
http://www.liveactionsafety.com/lma-supreme-airways/? gclid=CjwKCAjwoKDXBRAAEiwA4xnqvzY_RS3I4cAS4FjSneWr_5ErYqJO1OolgU31_72aKO3IM5vGNZWZjBoCG5gQ AvD_BWE; downloaded Jun. 12, 2018.
http://www.intersurgical.com/products/critical-care/water-traps; downloaded Jun. 12, 2018.
http://www.intersurgical.com/products/critical-care/flow-sensors; downloaded Jun. 12, 2018.
https://www.vyaire.com/us/our-products/respiratory-care/airway-management/suction-catheters-and-trach-care/tri-flo-subglottic-suction-system; downloaded Jun. 12, 2018.

* cited by examiner

LIQUID REMOVAL APPARATUS FOR A BREATHING CIRCUIT AND RELATED METHOD OF USE

BACKGROUND OF THE INVENTION

The present invention relates to breathing circuits, and more particularly to a liquid removal apparatus or device that is implemented in a breathing circuit to trap and/or remove condensate and secretions from the breathing circuit without having to open the breathing circuit.

Each year, approximately 4,000,000 people are admitted to intensive care units (ICU) in the United States. Approximately 1,000,000 of these cases require mechanical ventilation, with more than 40,000 of these patients dying each year due to Ventilator Associated Pneumonia (VAP). In addition to those who die, more than 200,000 patients contract VAP in the hospital. For those who survive, the duration of mechanical ventilation is extended by an average of 11 days and the duration of their hospitalization increases by about 25 days resulting in a substantial average cost to treat each case of VAP.

There are many suspected causes of VAP, however, experts agree that the aspiration of water and sputum are the most significant causes. Aspiration occurs when water, sputum or other fluids enter the lungs of the patient. For ventilated patients, the water condenses on the walls of the ventilator tubes because the air passing through the tubes is saturated with humidity to protect the patient's lungs or throat from drying out and sputum is ejected from the patient's throat into the ventilator tubes. Both can enter the patient's lungs whenever the patient or the ventilator tubes are moved. In addition, micro aspirations, that is, small amounts of water and sputum that slip past the cuff of the endotracheal tube, can occur when the patient or ventilator tubes are moved. Micro aspirations have recently come under scrutiny as a notable cause of VAP in patients.

To address the above issues, and similar issues with respirators and other related devices that assist individuals breathing, a caregiver will drain the breathing circuit of the device periodically. A conventional procedure for removing accumulated fluids in a breathing circuit is as follows. A caregiver first dons gloves and places a cloth or paper towel near a simple junction in the breathing circuit. The caregiver applies pressure to the circuit to separate an inlet tube from the junction, then twists the junction and inlet tube to deposit accumulated liquids into the towel for disposal. After the fluids are removed, the caregiver reconnects the inlet tube to the junction, then properly disposes of the gloves and towel with the drained liquid therein.

While this procedure does remove liquids from the breathing circuit, it is less than optimal. For example, because the process is manual, a caregiver must periodically check on the patient. Even with regular checking, it is possible that additional liquids accumulate and/or the patient is moved, thereby causing the patient to aspirate the liquids. Further, when the inlet tube is separated from the junction, this causes a loss of positive end-expiratory pressure (PEEP). In turn, these situations can lead directly to ventilator associated lung injury (VALI), such as "shearing injury" caused by the immediate repressurization after loss of PEEP and/or VAP as mentioned above. Multiple studies have shown that one in four ventilated patients develops VALI and/or VAP. In addition, the current procedure places additional stress on the breathing circuit, particularly where it includes a suction catheter assembly. This typically causes the patient discomfort. Because patients using these devices are among the most critically ill, such additional distress can worsen their condition and complicate treatment.

Further, the current procedure can result in biologically contaminated liquid being exposed to the environment, which can place caregivers and others in the vicinity at risk of potentially contracting diseases carried by the patient. Also, by opening the circuit, the patient is potentially exposed to any airborne biological contaminants in a room in which the patient is located. In addition, the circuit can be contaminated by opening it in an unsterile fashion. Finally, the current process also creates a fair amount of waste, including at least one pair of gloves, towels, and possibly a facemask with each draining of the circuit, which can occur twelve times per day, with the typical patient intubated for one to two weeks.

Accordingly, there remains room for improvement in the field of removing fluids, water and secretions from a breathing circuit associated with a ventilated or intubated patient, or other patient needing breathing assistance.

SUMMARY OF THE INVENTION

An apparatus to remove liquid from a ventilation system is provided. The apparatus can include a housing, a first port and a second port extending toward one another in an interior volume of the housing, separated from one another by a gap that is at least 5 mm in width, such that ventilating fluid transfers from the first port to the second port while secretions and condensate escape through the gap, to be trapped in the housing. An extraction port is included in floor of the housing so that accumulated liquids in the housing can drain out the extraction port, by gravity or suction, while minimizing positive end expiratory pressure (PEEP) loss in the ventilation system, and without substantially exposing caregivers to biological material in the drained liquid.

In one embodiment, the first port joins with a ventilator. The second port joins with an intubation tube coupled to a tracheostomy or endotracheal tube. The ventilator establishes the applied PEEP in the system and related circuit, which optionally can be set at 350 Pascal to 650 Pascal, or other pressures depending on the application. The loss due to the draining via the extraction port can be less than 175 Pascal.

In another embodiment, the apparatus can include a junction or a circuit wye that joins with the intubation tube. The second port can join with the junction. A closed suction catheter assembly including a connection end can be joined with the junction. The assembly can include a suction catheter and a sleeve positioned over the suction catheter and joined with the connection end. The suction catheter can be disposed in the sleeve and can be reciprocally movable through the connection end to apply a first suction to accumulated liquids in the intubation tube and/or the patient's airway and lungs.

In still another embodiment, the apparatus can include a drainage tube extending from the extraction port. A control valve can be in fluid communication with the drainage tube. A controller joined with the control valve can control the control valve such that suction is applied through the drainage tube to drain the accumulated liquid from the housing on a periodic basis at predetermined intervals.

In even another embodiment, the control valve can be programmed to apply suction to the housing for five seconds or other durations, over 5 to 15 minutes, or other durations, and can include an optional override button for performing an on-demand evacuation. When the optional control valve is included, caregivers can focus more on patient care and comfort issues because time will not be consumed in draining liquid from the ventilator system.

In yet another embodiment, the apparatus can couple to the drainage device, which can be a syringe. The syringe can be manually actuated to apply suction through the extraction tube and remove the accumulated liquids from the housing.

In a further embodiment, a method is provided. The method can include providing the liquid removal apparatus; joining the first port with a ventilator tube; joining the second port with a junction that is joined with an intubation tube; providing fluid flow through the housing to ventilate an intubated patient's airway with the ventilator and to establish an applied positive end expiratory pressure; and draining accumulated liquid from the housing through an extraction port in a lower portion of the housing, during the providing fluid flow step, such that the positive end expiratory pressure decreases insignificantly while the extraction port is in the open mode.

In still a further embodiment, the PEEP decreases by less than 15%, by less than 10% or by less than 5% while the extraction port is in the open mode, while accumulated liquid and secretions are drained from the ventilation circuit.

In still a further embodiment, the PEEP decreases by less than 150 Pa while the extraction port is in the open mode, or by less than 140 Pa while the extraction port is in the open mode, while accumulated liquid and secretions are drained from the ventilation circuit.

In yet a further embodiment, the method can include providing a closed suction catheter assembly including a connection end joined with the junction, a suction catheter and a sleeve positioned over the suction catheter and joined with the connection end; moving the suction catheter the sleeve and through the connection end to apply a first suction to accumulated liquids in at least one of the intubation tube and the patient to remove the accumulated liquids. The first suction can be distal from and inadequate to remove any of the accumulated liquids that gather in the liquid removal apparatus.

The current embodiments provide an apparatus and method for efficient and safe removal of accumulated liquids and secretions from a ventilation system circuit. The liquid extraction apparatus can reliably remove accumulated secretions, condensation and fluids from breathing circuits without significant PEEP loss. Further, where a controller and control valve is included, accumulated liquid evacuation can be performed automatically, that is, without the need for human intervention, thereby greatly reducing the likelihood of accidental aspiration of the accumulated fluids by the patient, particularly where a suction catheter assembly is utilized. Because both PEEP loss and aspiration of fluids are both significant contributors to negative outcomes for ventilated patients, the current embodiments can improve the quality of care for these patients. The apparatus also can be easily inserted into existing or conventional breathing circuit assemblies and to be easily connected to any of a variety of drainage devices for extracting fluid from the apparatus. The apparatus also can have a volume that sequesters liquids until they are evacuated from it without extra concern.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENTS

Figure 1:
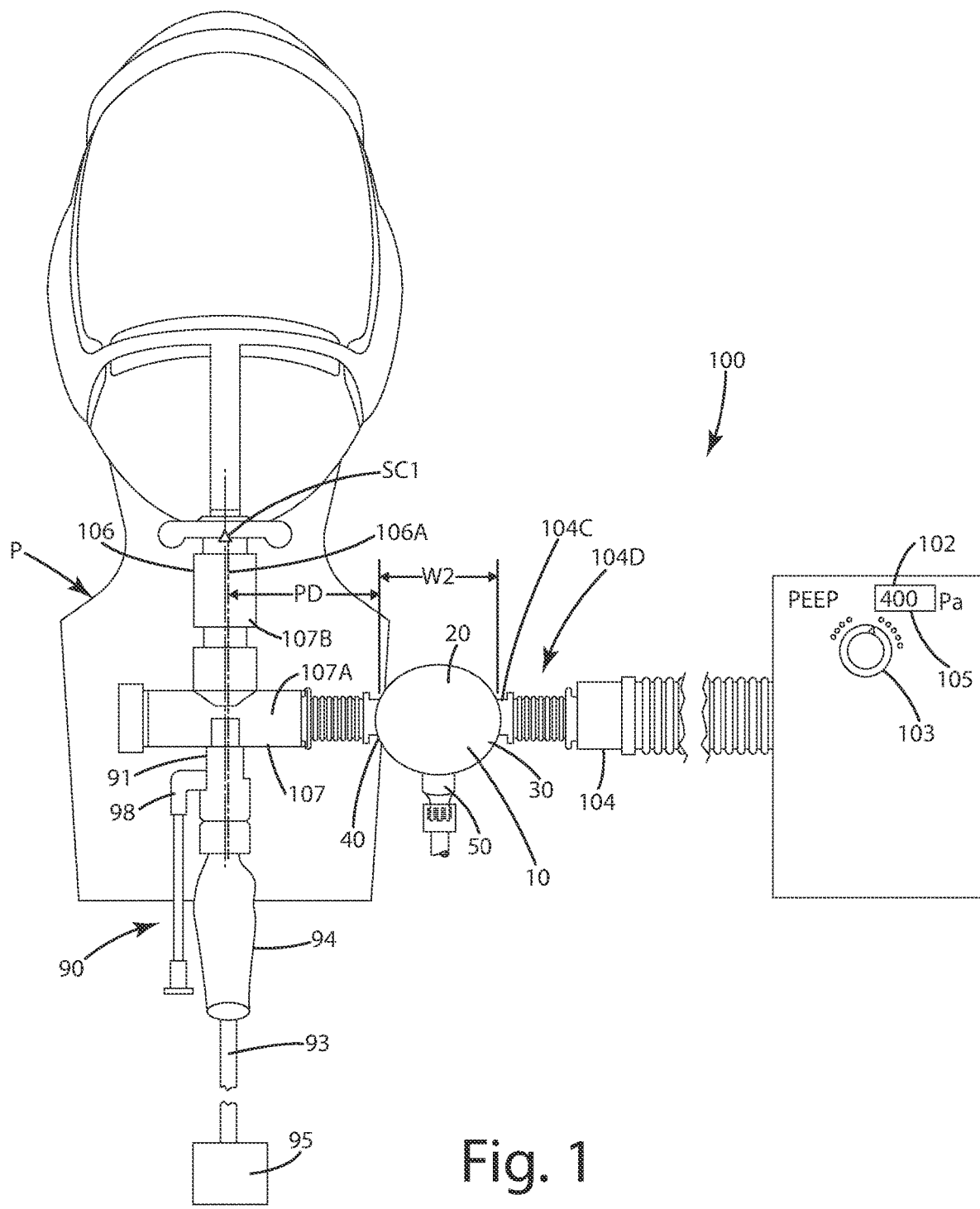
FIG. 1 is a perspective view of the liquid removal apparatus of a current embodiment installed in a ventilation system while the system is connected to an intubation tube installed in a patient's airway.
Figure 2:
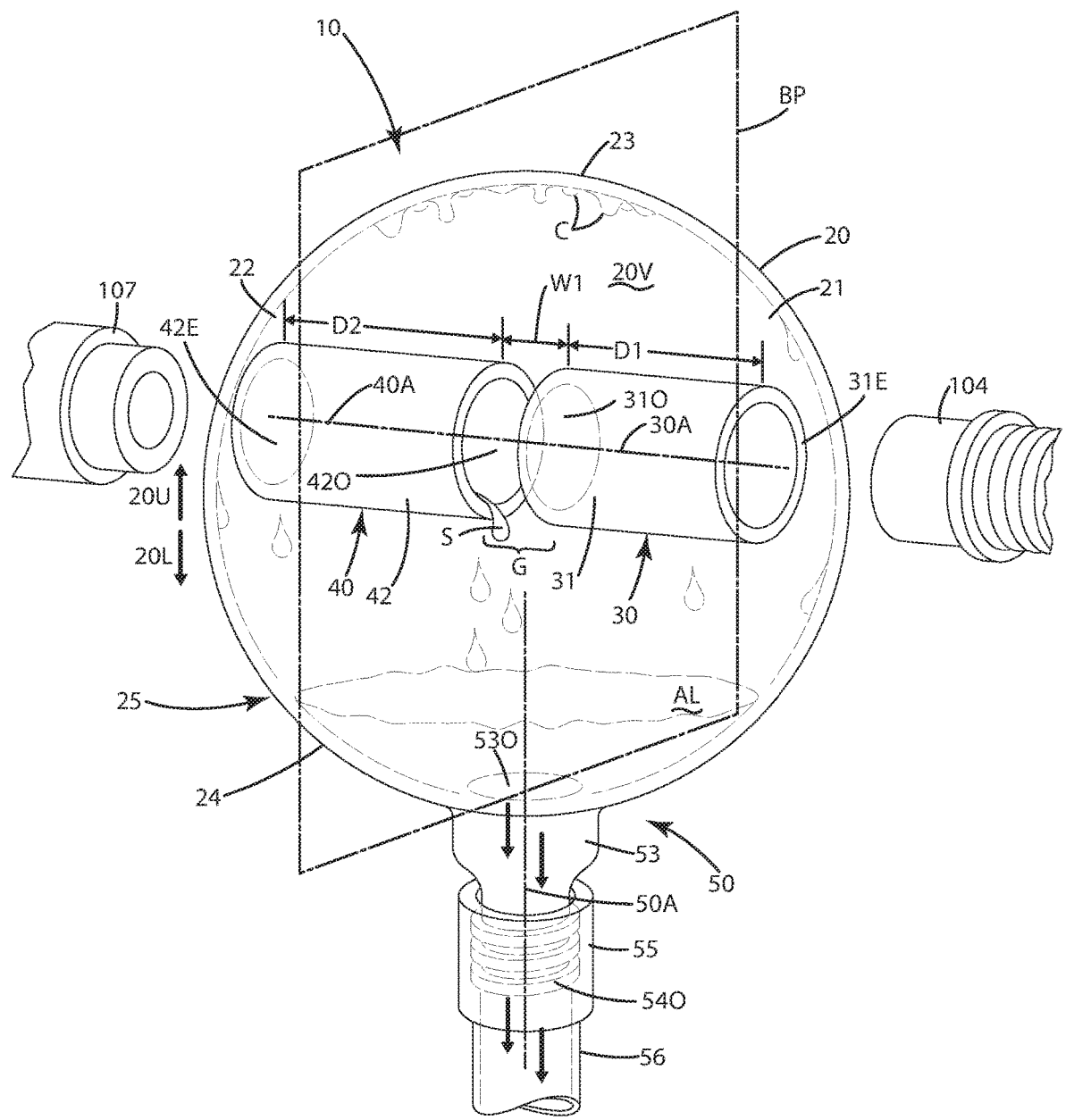
FIG. 2 is a perspective close-up view of the liquid removal apparatus.
Figure 3:
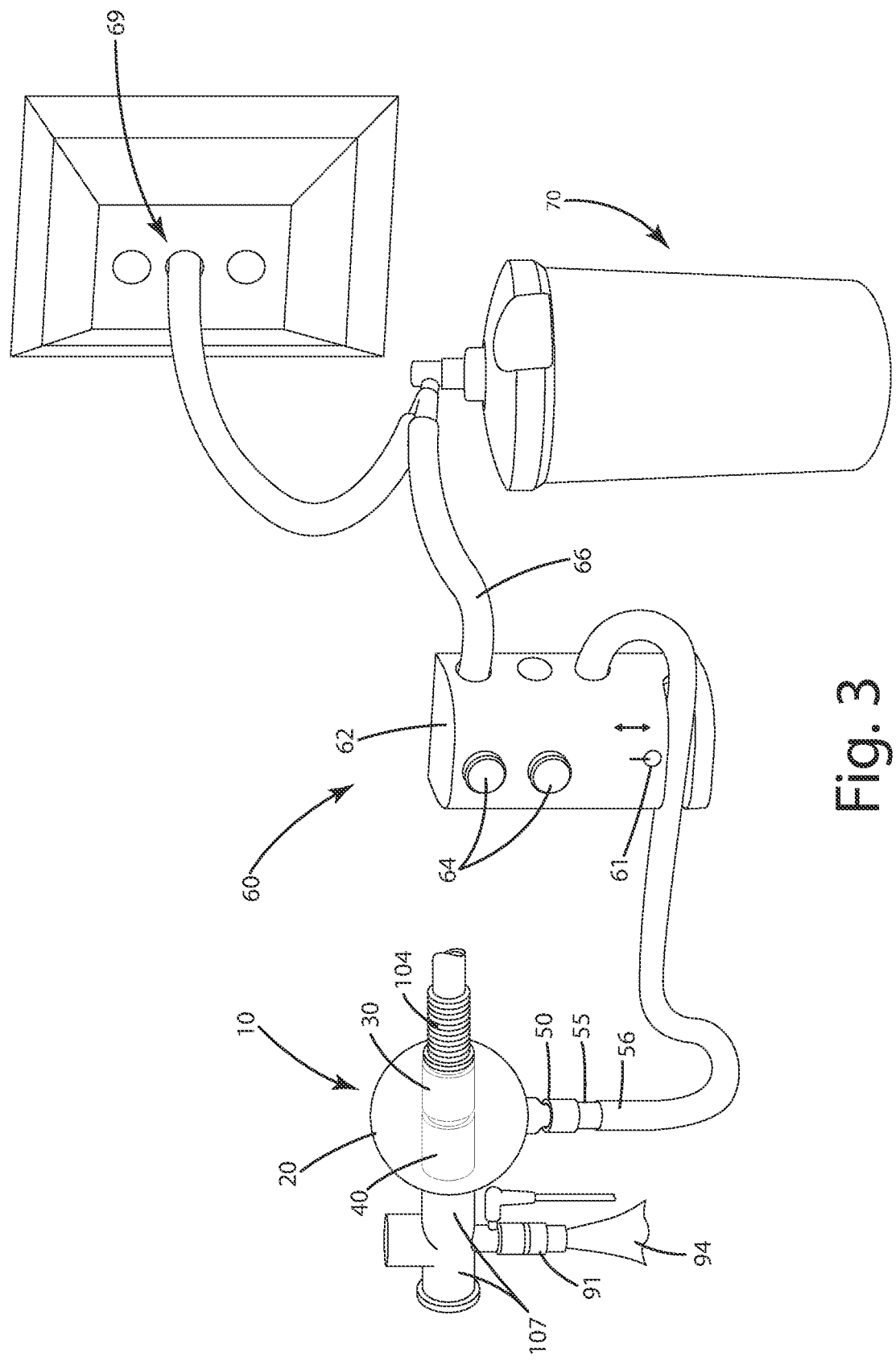
FIG. 3 is a perspective view of the liquid removal apparatus coupled to a drainage device including a controller and a control valve.

A current embodiment of the liquid removal apparatus is shown in FIGS. 1-3 and generally designated 10. The apparatus 10 is shown installed in a ventilation system 100, which includes a ventilator 102 that ventilates a patient P. Of course, the apparatus can be installed in any other type of breathing assistance system as well. The ventilator 102 can provide pressurized and humidified air including oxygen or other gases through the ventilator tube 104, through the apparatus 10 and ultimately to an intubation tube 106 which can be in fluid communication with the airway of the patient P via an endotracheal tube, tracheostomy or other conduit. The apparatus 10 is installed in close proximity to the intubation tube 106 to efficiently trap any secretions or accumulated liquids in the ventilation system so the patient does not aspirate the same. As used herein, "accumulated liquid" can refer to any condensate, liquid, water, secretion, sputum, foreign substance or material that may be present in the ventilation system. As used herein, "intubation tube" can include devices such as intubation tubes, tracheostomy tubes, endotracheal tubes and/or tracheostomies, that can facilitate transfer of air or fluids to the patient's airway so that adequate ventilation or support can be maintained.

Generally, the apparatus 10 includes a housing 20 defining an interior volume 20V, first port 30 in a first sidewall 21 of the housing and an opposing second port 40 in the second opposing sidewall 22 of the housing. The first port 30 includes an inwardly extending cantilevered first tube 31 and the second port 40 includes an inwardly extending cantilevered second tube 42 that are separated from one another in the interior volume by a gap G of a width W1 of at least 5 mm, or other amounts as described below. As used herein, the term "port" can be any conduit or opening into or through a component for the passage of an object, a liquid, a fluid and/or a gas. Fluids and gasses can flow through the tubes and cross the gap, providing fluid communication between the tubes and ports, so that the apparatus provides a consistent air flow via the ventilation system for the patient. Accumulated liquid that enters the housing from the humidified air or the patient side, however, is trapped in the interior volume 20V of the housing, and does not cross the gap G to transfer from one port to the other. In turn, this entrapped accumulated liquid drains down the walls of the housing and pools in the lower portion or near the lower floor portion 24 of the housing. There, the apparatus also includes an extraction port 50 including an extraction tube 53 so that accumulated liquid AL in the interior volume 20V drains through the lower floor portion 24, through the extraction tube 53 when the extraction port 50 is in an open mode. The extraction port 50 can be joined with a drainage device, such as a wall suction unit, suction canister, pump, and/or syringe as described below, to drain the accumulated liquid from the interior volume, all while maintaining decent pressure in the ventilation system or circuit 100 and preventing collapse of the patient's lungs, as well as exposing a caregiver to biological materials in the accumulated liquid AL. With the apparatus, significant amounts of condensate in the ventilation circuit 100 can be captured. Optionally, at least 75%, at least 80%, at least 85%, at least 90%, at least 95% or at least 98.8% of condensate in the circuit can be captured and drained with the apparatus.

While the liquid removal apparatus 10 and its components will be described below, the apparatus 10 as shown can be used in the context of a ventilation system or circuit 100, which can include a ventilator 102 and other components. The ventilator 102 can include a controller 103, which can set the extrinsic or applied pressure in the system, and can generally maintain or apply a particular positive end expiratory pressure (PEEP) in the ventilation system via the ventilator. Sensors in the system can monitor the PEEP and flow in the system and display the same on a display 105. In use, for typical ventilated patients, the pressure optionally can be set around 350 Pascal to 600 Pascal to ventilate the patient P with the system. This PEEP can be monitored by a caregiver during ventilation, as well as during use of the apparatus 10 during a draining sequence when the extraction port 50 is used for the same.

The extraction port of the apparatus 10 provides exceptional preservation of administered PEEP in the system 100. The apparatus 10 does not require any significant opening or breaking of the circuit or ventilation system to perform the draining. When the apparatus and extraction port are used, the decrease in PEEP can be minimized so that pressure in the patient's airway is generally maintained. As an example, even when the extraction port is used to drain accumulated liquid from the housing and ventilation system or circuit 100, the decrease or loss in PEEP caused by that draining and "opening" of the extraction port to an open mode can optionally be less than 175 Pascal, less than 150 Pascal, less than 125 Pascal, less than 100 Pascal, less than 75 Pascal, less than 50 Pascal, less than 25 Pascal or less than 5 Pascal, from a baseline PEEP in the ventilation system before the extraction port is opened. Using other comparative measurements, the decrease or loss in PEEP caused by the draining and "opening" of the extraction port to an open mode can optionally be less 25%, less than 20%, less than 15%, less than 10%, less than 5%, or less than 1% of a baseline PEEP and flow rates in the ventilation system before the extraction port is opened. In most cases, this small loss in PEEP is less than or the same as the loss in PEEP when a suction catheter is used to remove sputum or other accumulated liquid from the endotracheal tube and the patient's airway.

The ventilation system 100 with which the apparatus 10 is used can be any type of ventilation system or breathing circuit. With the simplicity of the apparatus, it can be plugged into the circuit 100 in several locations, but optionally close to the intubation tube to readily capture secretions and sputum from the patient to prevent aspiration. As shown, the system can include a first tube or ventilator tube 104 joined with the ventilator. The tube 104 can include a distal end 104D which can have a collar 104C. The collar 104C can be sized and dimensioned to slip-fit or friction fit in the first port 30, extending partially beyond the first sidewall 21 of the housing and into a first tube of the first port as described below. Of course, the distal end 104D can alternatively be threaded to, clipped to or over or around the first port 30 in other constructions. The system also can include a junction 107 that is joined with and secured to the intubation tube 106. The junction shown can be in the form of an elbow or wye or "T". The elbow can include a first elbow port 107A that can join with a tube or can be inserted into or over the second port 40 to join the junction with the housing of the apparatus. The elbow can include a second elbow port 107B that can join to the intubation tube 106.

Optionally, the junction 107 can further be joined with a closed suction catheter assembly 90 including a connection end 91 joined with the junction. The assembly 90 can include a suction catheter 93 and a sleeve 94 positioned over the suction catheter and joined with the connection end. The suction catheter 93 can be movably disposed in the sleeve and can be movable through the connection end and the junction so the distal end of the suction catheter can enter the intubation tube and in some cases the patient's airway. When inserted, the suction catheter 93 can apply a first suction to accumulated liquids in the intubation tube and the patient. That suction can be applied via the catheter suction source 95. That suction also can be separate and distinct from any suction applied through the extraction port of the apparatus 10 to remove accumulated liquids AL in the housing 20. It is noted that the suction catheter 93 also is generally incapable of removing the accumulated liquids that gather in the liquid removal apparatus herein.

As used herein, "suction catheter" can refer to an elongate tube, constructed from latex and other polymers, used to remove secretions from the airway and are available in many sizes, commonly from 5 to 20 French and varying lengths, typically from 15 to 25 inches (38 to 64 cm). The suction catheter can have a length that is sufficient to extend through the elbow and through any attached junction and through the intubation tube 106, along path SC1 and into a portion of a patient's airway or respiratory tract to suction secretions therefrom. When a suction force from the source 95 is discontinued, the suction catheter 93 can be withdrawn from the patient's airway and the tube 107, and is returned to its sleeve 94. In this manner, the length of the suction catheter 93 is contained within the sleeve 94 and it is therefore positioned outside of the closed ventilation system of the patient until needed again for suctioning secretions. Some types of closed suction catheter assemblies are available under the tradename TRACH CARE® from BALLARD® Medical Products.

Further optionally, the junction 107 or assembly 90 can include an administration port 98. This port can be configured to join with a syringe or other device to administer substances into the junction and thus into the intubation tube 106 and patient's airway. For example, the administration port can be used to administer a washing solution, a medication, a fluid and/or a lavage into the intubation tube.

As shown in FIG. 1, and as mentioned above, the apparatus 10 can be installed in close proximity to the intubation tube 106 to efficiently trap any secretions or accumulated liquids in the ventilation system so the patient does not aspirate the same. The farther the apparatus is from the intubation tube, the less secretions are trapped well, and/or preventatively by the apparatus. In this regard, the intubation tube 106 can include an intubation tube axis 106A. The second port 40 can be joined with the junction 107 so that the housing 20 of the apparatus. The junction or an associated tube can be sized and dimensioned to slip-fit or friction fit in the second port 40, extending partially beyond the second sidewall 22 of the housing and into a second tube of the second port as described below. Of course, the junction or associated tube can alternatively be threaded to, clipped to or over or around the second port 40 in other constructions.

The housing 20 and second port 40 can be disposed a preselected distance PD from the intubation tube axis. This preselected distance can be optionally less than 100 mm, less than 75 mm, less than 50 mm, less than 25 mm, or less than 10 mm away from an intubation tube axis of the intubation tube. With such spacing, the secretions and/or accumulated liquids can collect in the housing rather than in the intubation tube. Because the ventilation tube also enters the housing before the junction, the apparatus can also trap condensate from humidified air pushed by the ventilator toward the intubation tube. This way, the condensate and liquid in the ventilation fluid can be prevented or impaired from entering the patient's airway.

With reference to FIG. 2, the liquid removal apparatus 10 includes the housing 20, the first port 30 to the ventilator, the second port 40 to the intubation tube 106 and the extraction port 50. The housing 20 can define the interior volume 20V. The interior volume can be designed to hold a precise amount of anticipated accumulated liquids without adding too much weight to the ventilation system and circuit, which might pull on the intubation tube and/or cause discomfort to the patient P. In this regard, the housing and the components of the apparatus 10 can be constructed from a lightweight medical grade material, such as polymers including medical grade of polyvinyl chloride, polyethylene, polycarbonate, PEEK, Ultem PEI, polypropylene, polysulfone, polyurethane and others. The housing material also can produce smooth surfaces, which can be nonporous, to facilitate the movement of liquid and prevent accumulation of biological contaminants. The housing material can be treated with non-leaching antimicrobial agents.

The housing 20 can include a ceiling 23 in an upper portion and a floor 25 in a lower portion, the floor including a lower floor portion 24. The housing can include a first sidewall 21 and an opposing second sidewall 22 formed continuously with one another. The ceiling can be angled or can curve downwardly to the first sidewall and the second sidewall so that any condensate or liquid on the ceiling 23 rolls and/or is conveyed downward therefrom to the first and second sidewalls. The ceiling and walls can all be integrally formed with one another as a single piece unit, with no substantial deformations to impair liquid flow from the ceiling to the sidewalls. Optionally, the ceiling, sidewall and floor, and the housing in general can be of a spherical, curved or rounded shape, again to facilitate liquid flow toward the extraction port 50. The floor 25 can angle or curve in a downward direction toward a lower floor portion 24. In some cases, the floor can form a tapered or funnel shape to direct liquid downward under the force of gravity or suction toward the extraction port 50.

The housing 20 can define a bisecting plane BP between the first sidewall and the second sidewall. This bisecting plane BP can divide the housing into equal sized left and right halves, including the respective ports and sidewalls. Of course, in some applications the bisecting plane might divide the housing into dissimilar or differently shaped portions.

The apparatus 10 can include a first port 30 and a second port 40 as mentioned above. These components can be integrally formed with the respective first and second sidewalls as a single piece unit made from continuous piece of material such as a polymer. The first port 30 can include a first port axis 30A and a first tube 31 that extends inward from the first sidewall 21 into the interior volume 20V a first distance D1. That distance D1 can be less than the width W2 of the housing 20 in FIG. 1, and optionally less than the distance from the first sidewall 21 to the bisecting plane BP. The first tube 31 can extend inward toward the bisecting plane BP such that the first port axis 30A is orthogonal to the plane BP. The first tube 31 optionally can be disposed in the upper half 20U of the housing, rather than the lower half 20L in which the accumulated liquid can collect. The first tube 31 can include a first inner opening 31O that opens to the interior volume and a first outer opening 31E that opens adjacent the first sidewall. That first outer opening 31O can open at the exterior surface of the sidewall, or can extend farther away from the bisecting plane BP than the sidewall 21. The first outer opening can be located where the interior of the tube transitions to the exterior surface of the sidewall 21. The first outer opening 31E can be configured to join with the ventilator tube 104 as described above. Optionally, the first tube 31 can extend far enough into the volume 20V so that condensate and other liquids on the sidewalls and ceiling do not enter the port 30, yet so air and gases can transfer to the other port 40.

The second port 40 can include a second port axis 40A and a second tube 42 that extends inward from the second sidewall 22 into the interior volume 20V a second distance D2. That distance D2 can be less than the width W2 of the housing 20 in FIG. 1, and optionally less than the distance from the second sidewall 22 to the bisecting plane BP. The second distance D2 can be equal to the first distance D1 so that the first and second ports project equal distances from their respective sidewalls toward the bisecting plane. The second tube can extend toward the first tube, into the interior volume. The second tube 40 can include a second tube axis 40A. The second port axis and the first port axis can be coincident with one another, or at least aligned so that each axis extends into the inner opening of the other tube. The second tube 42 can include a second inner opening 42O that opens to the interior volume and a second outer opening 42E that opens adjacent the second sidewall. That outer opening can open at the exterior surface of the sidewall, or can extend farther away from the bisecting plane BP than the sidewall 22. The second outer opening 42E can be configured to join with the junction 107 or intubation tube 106 as described above. Optionally, the second tube 42 can extend far enough into the volume 20V so that condensate and other liquids on the sidewalls and ceiling do not enter the port 40, yet so air and gases can transfer to the other port 30, across the gap or generally from the interior volume into the other port.

As shown in FIG. 2, the second tube can be separated from the first tube by a gap G that has a width W1 that can be optionally at least 5 mm, at least 10 mm, at least 15 mm, at least 20 mm, at least 25 mm, at least 30 mm, at least 35 mm, at least 40 mm, at least 45 mm, or at least 50 mm. Again, this gap G can be sufficient so that humid air from the ventilator can escape the ports and condense as condensate C on the ceiling, and/or so that secretions S from the junction or intubation tube will drop into the volume, without transferring from the second port to the first port, and without re-entering the patient's airway. This gap G and its width W1 can be centered on the bisecting plane BP as shown, but in other applications, where the first and second tubes are of different lengths, the gap can be offset from the bisecting plane and/or transverse to it. The width and shape of the gap G also can be altered based on the inner openings of the tubes, and the inner portions of those tubes.

The first and second tubes 31 and 42 can provide several functions. For example, the first tube 31 can provide a load bearing surface to allow junction 107 to couple to the liquid removal apparatus 10. The second tube 42 can provide a load bearing surface to allow a ventilator tube to couple to the liquid removal apparatus 10. The first and second tubes can be rounded or circular at their inner dimension to facilitate this coupling, but can be of other cross sections depending on the application. The first tube 31 and second tube 42 can prevent liquids and secretions, which accumulate in the interior volume 20V, from reentering the system while the system is operating. The first tube and second tube can prevent liquid reentry into the system even when liquid removal apparatus 10 is moved or reoriented, relative to the junction, the ventilator tube and/or the patient, for example, due to patient being repositioned. The first and second tubes can prevent condensate such as water moving from the ventilator tube 104 (due to humidified air from the ventilator) and entering the second tube 142. The condensate C from water in humidified air can accumulate in the apparatus, for example, on the roof 23 and/or sidewalls until it drips or drains down the sidewalls to the floor, of course being diverted around the respective port openings via the first and second tubes. Likewise, the secretions S from junction 107 drip into or otherwise enter the gap G, and under the force of gravity can accumulate near the floor, below the ports and respective tubes. These secretions also are unable to move across gap G. The size of first and second tubes can drive the overall size of the apparatus 10, which can be specified to reduce weight in the breathing circuit or ventilation system 110. Optionally, the predetermined distances D1 and D2 by which the tubes project into the interior volume 20V in a cantilevered manner, in some cases referred to as the length of the tube, can be optionally about 1 to 3 times, inclusive, about 1.25 to 2.5 times, inclusive or about 1.5 times, the diameter or dimension of each of the respective tubes 31 and 42. Further optionally, the width W1 of gap G can be optionally about 1 to 3 times, inclusive, about 1.25 to 2.5 times, inclusive, or about 0.5 and 2 times or about 1.5 times, the diameter or dimension of each of the respective tubes 31 and 42. With this width, the air or gas can be effectively communicated between the first port and second port, while still allowing the condensate, water or other liquids to be removed from the ventilation tube, so the same does not enter the second tube. This width also can allow the secretions from the second port adequate space to exit the second tube and gather in the housing of the apparatus.

With further reference to FIG. 2, the liquid removal apparatus 10 can include an extraction port 50. This port can be integrally formed with the lower floor portion 24 of the housing, formed with the floor 25 as a single piece unit, continuous with the sidewalls 21 and 22. The extraction port 50 can include an extraction port axis 50A and an extraction tube 53. The extraction port axis 50A can project upward toward the ceiling 23. The axis 50A can lie within a bisecting plane BP of the housing. The axis 50A can project through the gap G between the first port tube and the second port tube. The axis 50A can be centered on the width W1. The axis 50A can be equal distanced from the openings 31O and 42O of the respective tubes.

The extraction port 50 can include an extraction opening 53O that opens adjacent the floor of the housing 20 to the interior volume 20V. The opening can open directly to the lower floor portion such that any accumulated liquid in the interior volume drains through it. The accumulated liquid AL can drain toward the extraction opening when the extraction port 50 is in an open mode, which simply means the port is opened somehow so that liquid can flow through it, for example under gravity or via suction force being applied to the extraction port to remove the accumulated liquid AL by some drainage device as described below. The extraction port 50 can include an extraction tube or hose 53 that extends outward form the housing 20 a distance to an extraction outer opening 54O. The extraction tube optionally can include a lower extraction tube portion that is threaded to receive a drainage device, fitting or adapter 55.

The extraction port 50 can be configured to join with a drainage device to drain at least one of accumulated liquid and secretions from the interior volume when the extraction port is in the open mode, as mentioned above, however, this drainage or removal of the accumulated liquids can occur without substantial loss of PEEP in the intubation tube and first tube joined with the ventilator while the extraction port is in the open mode.

Figure 4:
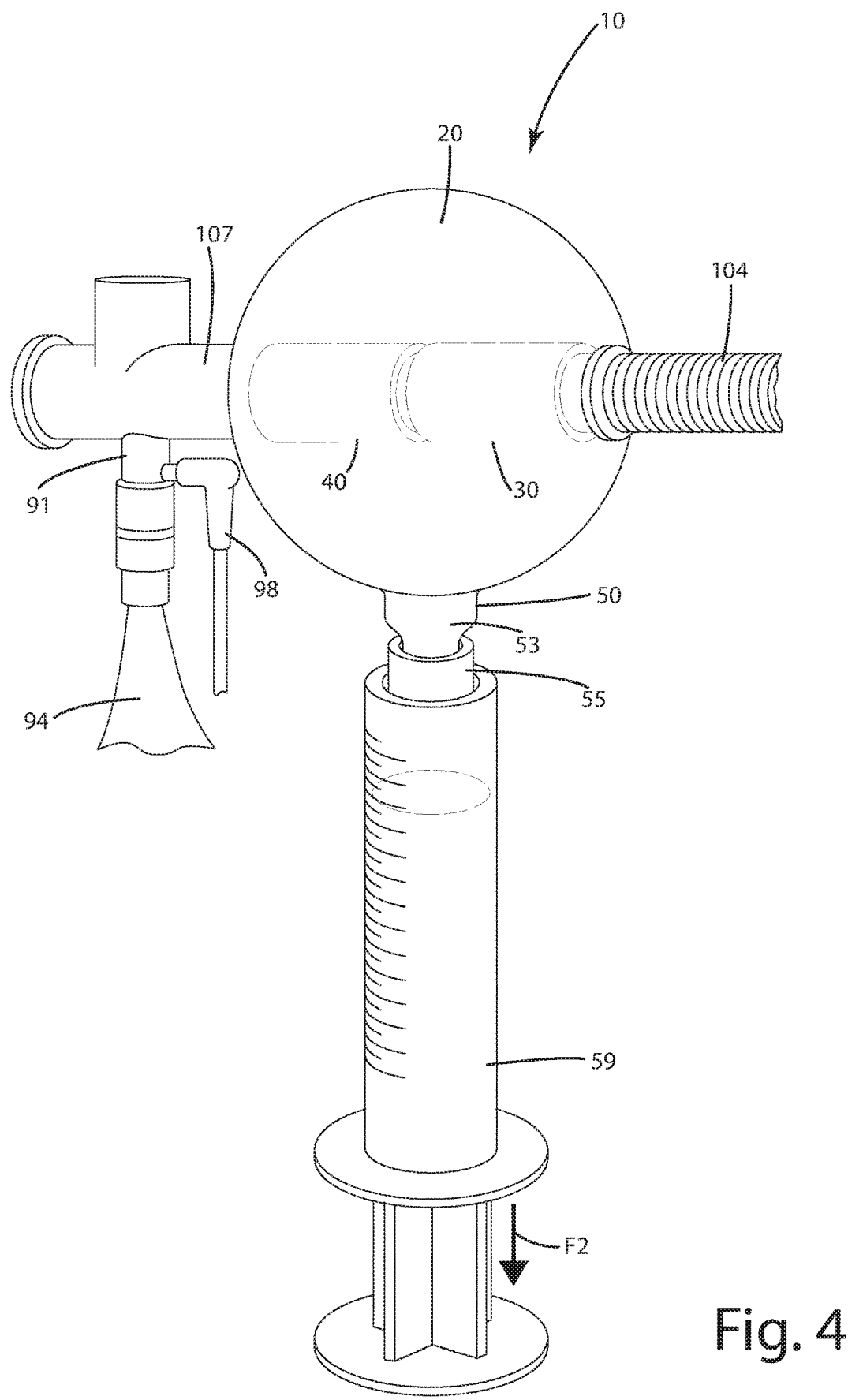
FIG. 4 is a perspective view of the liquid removal apparatus coupled to a drainage device including a syringe for manual draining of the liquid removal apparatus.
Figure 6:
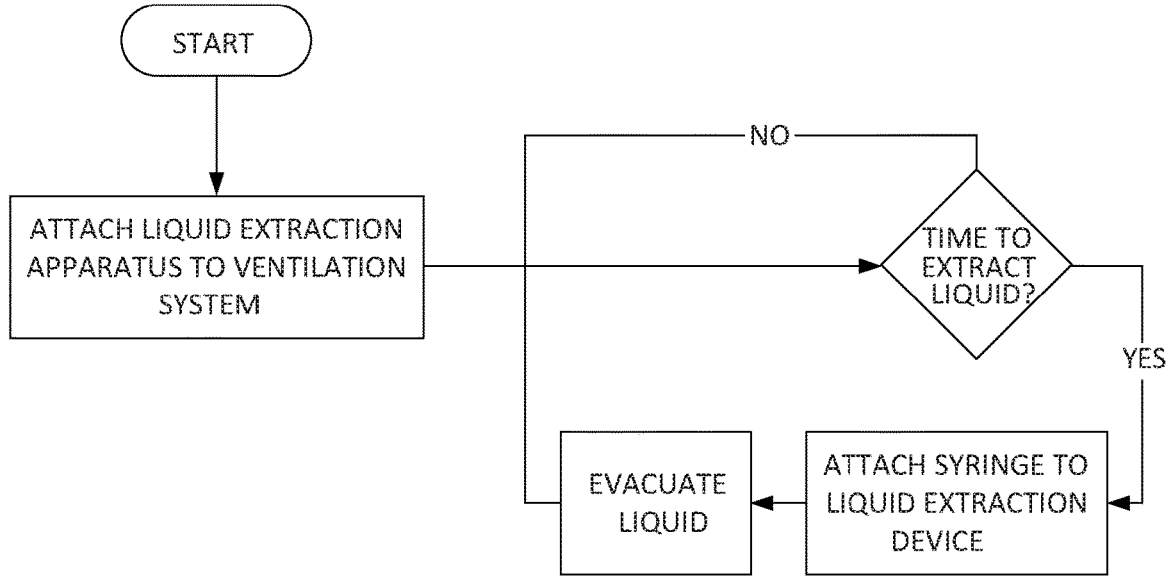
FIG. 6 is a flowchart of a manual process to drain the liquid removal apparatus with the drainage device in FIG. 4.

As shown in FIG. 4, a simple drainage device that can be connected to the extraction port 50 can be a syringe 59. When accumulated liquids AL have accumulated in the housing 20, a caregiver can attach the syringe 59 to a fitting or adapter 55 that is secured to the extraction port 50 or tube, which optionally can be threaded or stepped to accommodate different sized drainage tubes 56 depending on the application. The syringe 59 can be manually actuated to exert a force F2 and thus apply suction through the extraction tube and remove the accumulated liquids from the housing. The syringe can be operated to remove the accumulated liquids when the extraction port is in an open mode. The liquids can be removed without a notable loss in PEEP in the circuit or system 100. This process is shown in the flowchart of FIG. 6. There, the liquid removal apparatus 10 can be installed in a ventilation system. The extraction port 50 can be connected to adapter or fitting 55. The caregiver can compute whether it is time to extract fluids, such as accumulated liquid, from the housing 20. For example, the amount of accumulated liquid can be computed by multiplying the typical fluid accumulation rate by the time period between patient check-ups by a caregiver. The volume of the accumulated liquid, when ready for removal and drainage, can be optionally between 10 ml and 40 ml, inclusive, between 20 ml and 30 ml inclusive, or about 25 ml. If it is time to extract the above amounts of liquid, the caregiver can attach the syringe 59 as shown in FIG. 4, and can apply suction to evacuate or drain the accumulated liquid from the housing 20. Thereafter, the syringe can be removed until the next time the liquid is to be removed from the apparatus 10.

As shown in FIG. 3, another drainage device 60 can be associated with a suction port 69 common in hospital settings. The device 60 can include a drainage tube 56 extending from the extraction port 50. The drainage device 60 can include an automated control valve 61 joined with the drainage tube, and a controller 62 joined with the control valve and configured to control the control valve such that suction is applied through the drainage tube to drain the accumulated liquid from the housing on a periodic basis. The controller can include inputs 64, such as buttons, switches or toggles, which can provide manual override of the automatic control system, suction time interval setting, suction time setting, etc.

The drainage device can include another tube 66 in fluid communication with a suction canister 70, which is to a wall suction port 69. The controller 62 can control the control valve to apply suction from the port or source 69 to the drainage tube 56 so the extraction port 50 attains an open mode to drain the accumulated liquids on a periodic basis. The periodic basis can be optionally at least once per hour, at least once per 30 minutes, at least once per 15 minutes, at least once per 10 minutes, at least once per 5 minutes or at other time intervals depending on the application. With such operation, the accumulated liquid is automatically drained from the housing without manual intervention by a caregiver. Optionally, the controller 62 can be sensor-operated, that is, it can "turn on" the control valve when a sensor (not shown) deployed within the apparatus 10 or housing 20 indicates that the accumulated liquid has reached a particular level or volume or mass. The time of operation of the optional control valve 61 can be determined by dividing the volume at which the sensor triggers by the evacuation rate due to the suction applied via the port.

The control valve 61 can be any type of valve. Optionally, the control valve 61 can be in the form of a pinch valve, so that fluids moving through tube 56 stay contained within tube and do not contact the valve. Such pinch valves are also known as squeeze valves, rubber hose valves or rubber tube valves. These valves can use a pinching effect to obstruct fluid flow. In the drainage device 60, the pinch valve can be normally closed, such that the controller opens the valve to apply the suction from the port 69 to drain the apparatus 10. In other applications, the pinch valve can be normally open.

In devices where the pinch valve is normally closed, the pinch valve can compress the tubing and prevent any flow. At prescribed time intervals, the pinch valve is programmed to open and close in a specific pattern to drain the water from the reservoir while maintaining pressure in the ventilation system and preventing the collapse of the patient's lungs. Alternatively, the accumulated liquid in the apparatus 10 can be evacuated by pressing an input 64, which can be a manual override button, on the controller 62 to operate the pinch valve 61. When the button is pressed the valve opens so suction or vacuum can be applied to the evacuation port to remove or drain the accumulated liquids in the apparatus. By using the apparatus with such a drainage device 60, this can reduce the occurrence of VAP, prevent caregivers from being exposed to the patient's dangerous germs, and allow more time for hospital care givers to focus on patient care and comfort issues.

When the apparatus 10 is used with the drainage devices herein, such as that shown at 60, it does require any changes to current clinical practices. When a patient is being connected to a ventilator 102, the apparatus 10 is inserted into the system, a step that takes only seconds. The drainage tube 56 from the apparatus 10 can be routed through the controller with the valve, which can already be mounted in the room. The tube can be routed to a suction canister with multiple inlet ports, to avoid using a valuable suction line. Once the device is installed and the control valve is turned on, the system can be left unsupervised. Caregivers can continue to monitor the patient once every other hour, and can focus more on the patient's well-being instead of removing water from ventilator lines. Depending on the application, the apparatus 10 can be sized for the ventilation system.

Optionally, where the suction to the extraction port is continuous, the apparatus interior volume 20V can be minimized, on the order of 1 ml, since any liquids that accumulate in the volume can be immediately evacuated with the drainage device 60. Further optionally, the controller can operate the valve 61 on a timer, that is, it can "turn on" the valve periodically for a preset time, for example, for 10 seconds every 20 minutes or other intervals. In such cases, the interior volume can be determined by multiplying the typical fluid accumulation rate by the time period; and the preset time can be determined by dividing the volume by the evacuation rate. In these cases, the interior volume can be optionally 1 ml to 50 ml, inclusive, 5 ml to 25 ml, inclusive or 5 ml to 10 ml, inclusive.

Figure 5:
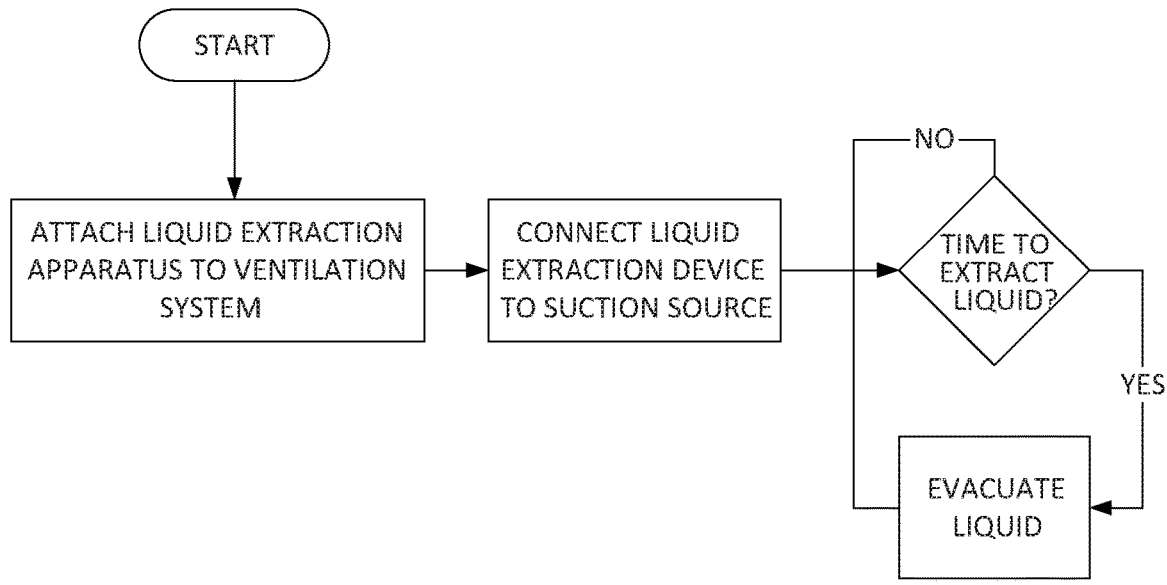
FIG. 5 is a flowchart of an automated process to drain the liquid removal apparatus with the drainage device in FIG. 3.

The drainage device of FIG. 4 can be operated according to the flowchart in FIG. 5 to prevent a patient from aspirating secretions and/or condensation. The liquid removal apparatus 10 can be inserted into the ventilation system 100 or circuit, optionally before or after a patient is connected to the breathing circuit. The tube 56 is directly or indirectly connected to the extraction port 50 and the source of suction 69, and optionally to the controller and control valve. At this point, the controller can be turned on. When on, the controller 62 can assess the need to evacuate accumulated liquid from housing 20 and apparatus 10 in general. In the case where optional control valve is operated based on a timer, evacuation can occur at the prescribed timer period. In the case where optional control valve is sensor-driven, evacuation can occur when the sensor (not shown) threshold is met. The controller can continue to loop, indefinitely, for as long as the drainage continues.

A method of using the liquid removal apparatus 10 will now be generally described in connection with the flowcharts mentioned above. The method can include installing the apparatus 10 in a ventilation system 100. The first port 30 can be joined with a ventilator tube 104 at the collar 104C, inserting the tube into the first tube 30, optionally so that the ventilator tube extends interior of the first sidewall 21. The second port 40 can be joined with the junction 107 that is joined with an intubation tube 106. That junction or a portion of it can be inserted into the second tube 40, optionally so that the portion 107 extends interior of the second sidewall. The ventilation system 100 can be operated to provide ventilation to the patient's airway. Fluid, such as humidified air and/or gases from the ventilator can flow through the housing to ventilate an intubated patient's airway with the ventilator and to establish an applied positive end expiratory pressure (PEEP). That PEEP can be set by the caregiver on the ventilator and displayed on the display 105 of the ventilator 102. Ventilation can continue, but as it does, liquid, water or condensate C from the humidified air can build inside the interior volume. Secretions S can be expelled from the patient and enter the interior volume of the apparatus.

The accumulated liquid AL can pool in the apparatus and its housing. The accumulated liquid can be drained from the housing 20 through an extraction port 50 in a lower floor portion of the housing, even while the ventilator 100 operates, using any of the drainage devices and associated processes described herein. During such removal and drainage of the accumulated liquid, the PEEP can decrease minimally, by any of the amounts mentioned herein, for example, by less than 15%, by less than 10% or by less than 5% while the extraction port is in the open mode, and the drainage occurs.

As mentioned above, the apparatus 10 can be installed in a system 100 that includes a closed suction catheter assembly 90 including a connection end 91 joined with the junction 107, a suction catheter 93 and a sleeve 94 positioned over the suction catheter and joined with the connection end. The suction catheter assembly, however, cannot typically remove the accumulated liquids from the system like the apparatus herein. The suction catheter can be used in a separate deep suction operation, in which the suction catheter 93 is inserted in the intubation tube and the patient's airway to remove accumulated liquids, such as secretions and sputum, there. The suction catheter can be moved through the connection end to apply suction to accumulated liquids the intubation tube and/or the patient's airway to remove the accumulated liquids. This suction can be separate and different from a suction applied to the extraction port 50 and apparatus 10 in general.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

In addition, when a component, part or layer is referred to as being "joined with," "on," "engaged with," "adhered to," "secured to," or "coupled to" another component, part or layer, it may be directly joined with, on, engaged with, adhered to, secured to, or coupled to the other component, part or layer, or any number of intervening components, parts or layers may be present. In contrast, when an element is referred to as being "directly joined with," "directly on," "directly engaged with," "directly adhered to," "directly secured to," or "directly coupled to" another element or layer, there may be no intervening elements or layers present. Other words used to describe the relationship between components, layers and parts should be interpreted in a like manner, such as "adjacent" versus "directly adjacent" and similar words. As used herein, the term "and/or" includes any and all combinations of one or more of the associated listed items.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative.

Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, any combination of X, Y and Z, for example, X, Y, Z; X, Y; X, Z; Y, Z, and/or any other possible combination together or alone of those elements, noting that the same is open ended and can include other elements.

What is claimed is:

1. A ventilation system liquid removal apparatus comprising:
    a housing defining an interior volume, the housing including a ceiling, a floor, a first sidewall and an opposing second sidewall, the floor extending in a downward direction toward a lower floor portion;
    a first port in the first sidewall, the first port including a first tube that extends inward a first distance from the first sidewall into the interior volume in a cantilevered manner, the first port configured to join to a ventilator tube joined with a ventilator;
    a second port in the second sidewall, the second port including a second tube that extends inward a second distance from the second sidewall, toward the first tube, into the interior volume in a cantilevered manner, the second tube separated from the first tube by a horizontal gap that is at least 5 mm in length, the second port configured to join with a junction that is joined with an intubation tube; and
    an extraction port in the lower floor portion of the housing, the extraction port including an extraction tube so that an accumulated liquid in the interior volume drains through the lower floor portion and through the extraction tube when the extraction port is in an open mode, the extraction port configured to join with a drainage device to drain the accumulated liquid from the interior volume when the extraction port is in the open mode,
    wherein the first port and second port are in fluid communication with one another to provide fluid flow through the housing and ventilation of an intubated patient's airway,
    whereby the accumulated liquid can be drained from the housing through the extraction port without substantial loss of positive end expiratory pressure in the intubation tube and ventilation tube joined with the ventilator while the extraction port is in the open mode.

2. The apparatus of claim 1,
    wherein the second port is joined with the junction so that the housing is less than 75 mm away from an intubation tube axis of the intubation tube,
    whereby the accumulated liquid accumulates in the housing rather than in the intubation tube.

3. The apparatus of claim 1,
    wherein the second port is joined with the junction so that the housing is less than 50 mm away from an intubation tube axis of the intubation tube.

4. The apparatus of claim 1,
    wherein the junction is an elbow,
    wherein the elbow includes a first elbow port configured to be inserted into the second port, wherein the elbow includes a second elbow port configured to join with the intubation tube,
wherein the elbow includes a lower portion joined with a sleeve,
wherein a suction catheter is movable into the elbow through the lower portion and into the intubation tube while the housing is joined with the elbow.

5. The apparatus of claim 4,
wherein an administration port is joined with the elbow,
wherein the administration port is configured to join with a syringe to administer at least one of a washing solution, a medication, a fluid and a lavage into the intubation tube.

6. The apparatus of claim 1 comprising:
a drainage tube extending from the extraction port,
a control valve joined with the drainage tube; and
a controller joined with the control valve and configured to control the control valve such that suction is applied through the drainage tube to drain the accumulated liquid from the housing on a periodic basis.

7. The apparatus of claim 6,
wherein the periodic basis is at least once per hour so that the accumulated liquid is automatically drained from the housing at least once per hour.

8. The apparatus of claim 1,
wherein the extraction tube extends downward from the floor and externally from the housing,
wherein the extraction tube includes a lower extraction tube portion that is threaded to receive the drainage device.

9. The apparatus of claim 8,
wherein the drainage device is a syringe,
wherein the syringe is configured for manual actuation to apply suction through the extraction tube and remove the accumulated liquid from the housing.

10. The apparatus of claim 1,
wherein the ceiling is curved and transitions to the first sidewall and second sidewall at curved transition regions,
wherein the extraction port includes an extraction port axis that lies within a bisecting plane of the housing and projects through the horizontal gap, and between the first tube and the second tube.

11. A ventilation system liquid removal apparatus comprising:
a housing defining an interior volume, the housing including a ceiling, a floor, a first sidewall and an opposing second sidewall formed continuously with one another, the ceiling curving downwardly to the first sidewall and the second sidewall, the floor curving in a downward direction toward a lower floor portion, the housing defining a bisecting plane between the first sidewall and the second sidewall;
a first port integrally formed with the first sidewall, the first port including a first port axis and a first tube that extends inward a first distance from the first sidewall into the interior volume, the first tube including a first inner opening that opens to the interior volume and a first outer opening that opens adjacent the first sidewall, the first outer opening configured to join with a ventilation tube joined with a ventilator;
a second port integrally formed with the second sidewall, the second port including a second port axis and a second tube that extends inward a second distance from the second sidewall, toward the first tube, into the interior volume, the second tube separated from the first tube by a gap that is at least 5 mm in width, the second port axis and the first port axis being coincident with one another, the second tube including a second inner opening that opens to the interior volume and a second outer opening that opens adjacent the second sidewall, the second outer opening configured to join with a junction that is joined with an intubation tube; and
an extraction port integrally formed with the lower floor portion of the housing, the extraction port including an extraction port axis and an extraction tube including an extraction opening that opens adjacent the floor of the housing to the interior volume such that at least one of an accumulated liquid and secretions in the interior volume drains toward the extraction opening when the extraction port is in an open mode, the extraction port including an extraction outer opening, the extraction port configured to join with a drainage device to drain the at least one of accumulated liquid and secretions from the interior volume when the extraction port is in the open mode,
wherein the first port and second port are in fluid communication with one another to provide fluid flow through the housing and ventilation of an intubated patient's airway,
whereby the at least one of accumulated liquid and secretions can be drained from the housing through the extraction port without substantial loss of positive end expiratory pressure in the intubation tube and ventilation tube joined with the ventilator while the extraction port is in the open mode.

12. The apparatus of claim 11,
wherein the junction is joined with a sleeve,
wherein a suction catheter is disposed in the sleeve and is movable through the junction into the intubation tube and to apply a first suction to draw accumulated liquid from at least one of the intubation tube and the patient.

13. The apparatus of claim 12,
wherein the drainage device includes a controller that controls a control valve to apply a second suction to the extraction port to drain the at least one of accumulated liquid and secretions from the housing.

14. The apparatus of claim 13,
wherein the controller is configured to control the control valve such that suction is applied to drain the at least one of accumulated liquid and secretions from the housing on a periodic basis,
wherein the periodic basis is at least once per hour so that the at least one of accumulated liquid and secretions is automatically drained from the housing at least once per hour.

15. The apparatus of claim 11,
wherein the second port is joined with the junction so that the housing is less than 75 mm away from an intubation tube axis of the intubation tube,
whereby the at least one of accumulated liquid and secretions accumulates in the housing rather than in the intubation tube.

16. The apparatus of claim 11 comprising:
a closed suction catheter assembly including a connection end joined with the junction, a suction catheter and a sleeve positioned over the suction catheter and joined with the connection end,
wherein the suction catheter is disposed in the sleeve and is movable through the connection end to apply a first suction to the accumulated liquid in at least one of the intubation tube and the patient.

17. A method of using an apparatus to remove liquid from a ventilation system, the method comprising:
   providing a liquid removal device including a housing defining an interior volume, a first port having a first tube that extends inward a first distance from a first sidewall into the interior volume in a cantilevered manner, a second port having a second tube that extends inward a second distance from a second opposing sidewall, toward the first tube, into the interior volume in a cantilevered manner, the second tube separated from the first tube by a horizontal gap that is at least 5 mm in length;
   joining the first port with a ventilator tube that is joined with a ventilator;
   joining the second port with a junction that is joined with an intubation tube;
   providing fluid flow through the housing to ventilate an intubated patient's airway with the ventilator and to establish an applied positive end expiratory pressure; and
   draining accumulated liquid from the housing through an extraction port in a lower floor portion of the housing while providing the fluid flow such that the positive end expiratory pressure decreases by less than 15% while the extraction port is in an open mode and the accumulated liquid is drained.

18. The method of claim 17,
   wherein the positive end expiratory pressure decreases by less than 10% while the extraction port is in the open mode.

19. The method of claim 18 comprising:
   wherein the positive end expiratory pressure decreases by less than 5% while the extraction port is in the open mode.

20. The of method of claim 17 comprising:
   providing a closed suction catheter assembly including a connection end joined with the junction, a suction catheter and a sleeve positioned over the suction catheter and joined with the connection end; and
   moving the suction catheter and the sleeve through the connection end to apply a first suction to the accumulated liquid in at least one of the intubation tube and the patient to remove the accumulated liquid.

* * * * *